US008488851B2

(12) United States Patent
Artal Soriano et al.

(10) Patent No.: US 8,488,851 B2
(45) Date of Patent: Jul. 16, 2013

(54) SYSTEM AND METHOD FOR MEASURING LIGHT SCATTERING IN THE EYEBALL OR EYE REGION BY RECORDING AND PROCESSING RETINAL IMAGES

(75) Inventors: Pablo Artal Soriano, Barcelona (ES); Jaume Pujol Ramo, Barcelona (ES); Sergio Oscar Luque, Barcelona (ES); Antonio Benito Galindo, Barcelona (ES); Guillermo Pérez Sanchez, Barcelona (ES)

(73) Assignee: Universitat Politecnica de Catalunya, Barcelona (ES)

( * ) Notice: Subject to any disclaimer, the term of this patent is extended or adjusted under 35 U.S.C. 154(b) by 639 days.

(21) Appl. No.: 12/598,834

(22) PCT Filed: May 5, 2008

(86) PCT No.: PCT/ES2008/000310
§ 371 (c)(1),
(2), (4) Date: Mar. 8, 2010

(87) PCT Pub. No.: WO2008/135618
PCT Pub. Date: Nov. 13, 2008

(65) Prior Publication Data
US 2010/0195876 A1 Aug. 5, 2010

(30) Foreign Application Priority Data

May 4, 2007 (ES) .................................. 200701267

(51) Int. Cl.
*G06K 9/00* (2006.01)
*A61B 3/00* (2006.01)
(52) U.S. Cl.
USPC ............................ 382/128; 351/211; 351/222
(58) Field of Classification Search
USPC ........................................................ 382/128
See application file for complete search history.

(56) References Cited

U.S. PATENT DOCUMENTS

| 7,699,471 | B2 * | 4/2010 | Lai | 351/222 |
| 7,891,812 | B2 * | 2/2011 | Larichev et al. | 351/211 |
| RE42,782 | E * | 10/2011 | Molebny et al. | 351/212 |
| 2003/0028115 | A1 | 2/2003 | Thomas | |

FOREIGN PATENT DOCUMENTS

ES  2 265 225  2/2007

OTHER PUBLICATIONS

Gerald Westheimer and Junzhong Liang, Evaluating diffusion of Light in the Eye by Objective Means, Apr. 1994, Investigative Ophthalmology & Visual Sciences, vol. 35, No. 5.*
Westheimer et al., "Evaluating Diffusion of Light in the Eye by Objective Means," Investigative Ophthalmology & Visual Science, Apr. 1994, vol. 35, No. 5, pp. 2652-2657.
International Search Report for PCT International Application No. PCT/ES2008/000310 mailed Oct. 6, 2008.

* cited by examiner

*Primary Examiner* — Hiep V Nguyen
(74) *Attorney, Agent, or Firm* — RatnerPrestia

(57) ABSTRACT

The invention relates to a system and method for measuring light diffusion in the eyeball or eye region, by recording and processing retinal images. The inventive system includes a double-pass ophthalmoscopic system having means for correcting low-order aberrations. Said system can be used to record images of the plane of the retina on a CCD camera, the outer part of said images containing information relating to ocular scattering. The aforementioned images can be used to obtain the objective scattering index (OSI), providing the ratio between the energy on the outer part of the image and the energy in the central part, or, alternatively, the modulation transfer function (MTF) area can be used for this purpose once the low frequencies have been filtered. According to the inventive method, the low-order aberrations are corrected before a retinal image or a temporal sequence of retinal images is captured and recorded.

17 Claims, 5 Drawing Sheets

SYSTEM AND METHOD FOR MEASURING LIGHT SCATTERING IN THE EYEBALL OR EYE REGION BY RECORDING AND PROCESSING RETINAL IMAGES

This application is a U.S. National Phase Application of PCT Application No. PCT/ES2008/000310, filed May 5, 2008.

FIELD OF THE INVENTION

The invention herein described is comprised within the field of visual optics, ophthalmology and optometry. In this field, the most important applications are targeted at studies on the aging of the visual system, the early detection and improved diagnosis of pathologies, especially of cataracts, following up on patients subjected to refractive surgery or patients with intraocular lens implants.

The present invention generally relates to a system and a method for measuring light scattering in the eyeball or eye region by recording and processing retinal images resulting from the reflection of a point light beam projected in the retina of a patient, and particularly to a system and a method which enable obtaining and processing images free of the influence of low-order aberrations.

BACKGROUND OF THE INVENTION

The retinal image of the human eye can deteriorate due to three causes: diffraction, aberrations and intraocular scattering. Diffraction is a property of the electromagnetic waves making up light and will consequently always be present in the retinal image. Its effect depends on the size of the pupil of the eye, being considerable only for small pupils (of the order of 2 mm or less), which virtually never occurs in normal vision conditions. The presence of aberrations and scattering in eyes of young subjects with normal visual conditions is low, but it increases considerably with age, the presence of ocular pathologies and refractive surgery interventions (I. IJspeert, J. K., de Waard, P. W., van der Berg, T. J., de Jong, P. T. (1990). The intraocular straylight function in 129 healthy volunteers: dependence on angle, age and pigmentation. Vision Research, 30(5), 699-707, Brunette, I., Bueno, J. M., Parent, M., Hamam, H., Simonet, P. (2003). Monochromatic aberrations as a function of age, from childhood to advanced age. Investigative Ophthalmology & Visual Science, 44, 5438-5446). Intraocular scattering in particular very significantly increases above normal values if ocular media transparency losses occur, such as those taking place in the crystalline with the development of cataracts.

The joint contribution of optical aberrations and intraocular scattering affects the quality of the retinal image. The double-pass technique (J. Santamaria, P. Artal, J. Bescos, "Determination of the point-spread function of human eyes using a hybrid optical-digital method", J. Opt. Soc. Am. A, 4, 1109-1114 (1987)) based on projecting a collimated light beam in the retina of the patient, and directly recording the light reflected therein after the double-pass of the light through the ocular media allows obtaining the objective measurement of the contribution of aberrations and scattering to ocular optical quality (F. Díaz-Doutón, A. Benito, J. Pujol, M. Arjona, J. L. Güell, P. Artal, "Comparison of the retinal image quality obtained with a Hartmann-Shack sensor and a double-pass instrument", Inv. Ophthal. Vis. Sci., 47, 1710-1716 (2006)).

Knowledge of the existence of ocular aberrations dates back to the middle of the 19$^{th}$ century. Low-order aberrations (defocus and astigmatism) can be measured using objective or subjective techniques and can be corrected using conventional lenses, contact lenses or refractive surgery interventions. Their impact on visual quality after their correction is therefore very low.

For measuring mid- and high-order (comatic, spherical . . . ) aberrations, different subjective and objective methods have been developed. There are currently several instruments based on these techniques which are used on a clinical level.

With respect to measuring intraocular scattering, there is no widely accepted robust method which allows the objective measurement thereof on a clinical level.

To date, most determinations of intraocular scattering have been performed using subjective methods of measurement. For example, the sensitivity to glare can be quantified by means of the equivalent background luminance (Stiles, W S. (1939) Discussion on disability glare at the 1939 CIE meeting in Scheveningen. Sekretariatsberichte der Zehnten Tagung CIE, 1942; Band I: 183-201, Vos, J. J. (2003). On the cause of disability glare and its dependence on glare angle, age and ocular pigmentation. Clinical and Experimental Optometry 2003; 86: 6: 363-370) technique based on the fact that the effect of the light scattered in the retina can be equaled by means of a background luminance and that it has led to the proposal of an equation for its quantification by the CIE (Comision Internacional de l'Eclaraige).

The direct compensation method is based on presenting an annular glare source with oscillating intensity and the compensation of its effect in the fovea through a central source of variable oscillating intensity in contrast with respect to that of the glare source. The straylight meter developed by Van der Berg is based on this method (Van den Berg, T. J. T. P. and Ijspeert, J. K. (1992). Clinical assessment of intraocular stray light. Applied Optics, 31, 3694-6).

The brightness visual acuity tester (Holladay, J. T., Prager, T., Trujillo, J., R. Ruiz. (1986). Brightness acuity test and outdoor visual acuity in cataract patients. Presented in part at the Symposium on Cataract, IOL and Refractive Surgery, Los Angeles.) is used to measure visual sensitivity and the power to discern between glare sources. It consists of an internally illuminated hemisphere with a hole in the middle. The patient holds the instrument close to his or her eye and observes a test through the hole. The latter provides a uniform glare source which can be used together with contrast sensitivity or visual acuity tests or charts.

Subjective methods have also been used which are combined with measurements of visual acuity and contrast sensitivity (J. Bailey, M. A. Bullimore (1991) A new test for the evaluation of disability glare. Optometry and Vision Science 68, 911-917). This type of measurement requires the active participation of the patient and can depend on many factors. Consequently, they are difficult and cumbersome to apply in clinical practice.

In addition, ophthalmologists normally use the slit lamp for routine cataract observation. A completely subjective method of classification and analysis has been developed using this observation (LOCS (Lens Opacities Classification System) III method (Chylack, L. T., Wolf J. F., Singer D. M., Leske, M. C., Bullimore, M. A., Bailey I. L., Friend, J., McCarthy, D., Wu, S. Y. (1993) The Lens Opacities Classification System III. Archives of Ophthalmology, 111, 831-836). Ophthalmologists must be specialized in this type of classification and results may differ among professionals. It must be taken into account that quantifying the grade of the cataract is of great interest for being able to determine the proper time to perform surgical intervention.

In recent years, methods have been developed to objectively determine intraocular scattering. However, most objective techniques and methods used are theoretical or experimental but not suitable for being adapted to a clinical setting, primarily due to the need to restrict variables affecting the measurement. In other words, the conditions in which the measurement is performed cannot be transferred to clinical practice as of today. It is possible to mention, for example, the dynamic light scattering measurement (Ansari, R. R., Datiles, M. (1999). Use of Dynamic Light Scattering and Scheimpflug Imaging for the Early Detection of Cataracts. Diabetes Technology and Therapeutics, 1(2), 159-168, Datiles, M., Ansari, R. R., Reed, G. F. (2002). A clinical study of the human lens with a dynamic light scattering device, Exp. Eye Res., 74, 93-102) or Scheimpflug imaging (Datiles, M., Magno, B., Friedlin, V. (1995). Study of nuclear cataract progression using the national Eye Institute Scheimpflug system, British Journal of Ophthalmology, 79, 527-534).

The double-pass (DP) technique by recording the image of a point on the retina contains information about aberrations and scattering. The contribution of the aberrations is located in the central part of the image, such that the more aberrated the eye is, the larger this central part. The effect of scattering is located basically in the outermost areas of the image such that the greater the scattering, the larger the peripheral image will be. Westheimer (Westheimer, G., Liang, J. (1994). Evaluating Diffusion of Light in the Eye by Objective Means. Investigative Ophtalmology and Visual Science, 35(5), 2652-2657, Westheimer, G., Liang, J. (1995). Influence of ocular light scatter on the eye's optical performance, J. Optical Society of America, 12(7), 1417-1424) combined subjective and objective measurements, verifying that intraocular scattering increases with age. Double-pass images were used in the objective part and a light scattering index was defined. However, the method developed was not robust to allow use on a clinical level. One of the main drawbacks of this technique is that the measurement is highly dependent on ocular aberrations. This is because the double-pass images are affected by both ocular aberrations and by intraocular scattering.

The use of a polarimetric technique by incorporating a polarimeter to a DP system to evaluate scattering has recently been suggested (Bueno, J. (2002). Polarimetry in the human eye using an imaging linear polariscope. Journal of Optics A: Pure and Applied Optics. 4, 563-561, Bueno, J., Berrio, E., Artal, P. (2003). Aberro-polariscope for the human eye, Optics Letters, 28(14), 1209-1211). This technique is based on the fact that light due to intraocular scattering is depolarized, whereas that forming the image in the retina maintains its polarization. Therefore, by evaluating the degree of depolarization of the light it is possible to evaluate the degree of intraocular scattering. However the low depolarization level of the retina for scattered light makes the application of the method unfeasible in clinical practice.

It must finally be pointed out that using the size of the spots of the Hartmann-Shack images has also been proposed for analyzing intraocular scattering (Applegate, R. A., Thibos, L. N. (2000) Localized measurement of scatter due to cataract. Investigative Ophthalmology and Visual Sciences (suppl), 41, S3).

All the systems and methods proposed for the objective evaluation of intraocular scattering are not robust, there still being no effective method for being used on a clinical level. In this context, it is undoubtedly advantageous to propose a new system and method for measuring light scattering in the eyeball or eye region, which can be readily adapted to clinical instrumentation. In fact, the new system and method presented allow objectively quantifying the degree of intraocular scattering and classifying the degree of development of a cataract, as well as objectively quantifying the degree of light scattering in the eye region caused by the tear film quality coating the cornea.

DESCRIPTION OF THE INVENTION

In a first aspect, the present invention relates to a system for measuring light scattering in the eyeball or eye region, conventionally comprising:
means for projecting a point light beam in the retina of an eye of a patient; and
recording means for recording an image of the plane of the retina resulting from the reflected light of said point light in the retina.

Generally, said means for projecting a point light beam and said recording means are part of a double-pass ophthalmoscopic system.

Unlike the known proposals, the system proposed by the present invention comprises means for correcting low-order aberrations of the eye prior to said recording so that said image of the plane of the retina is free of the influence of said low-order aberrations.

Generally, said means for correcting low-order aberrations are provided for correcting defocus and/or astigmatism aberrations.

A second aspect of the present invention relates to a method for measuring light scattering in the eyeball or eye region, comprising in a known manner:
projecting a point light beam on the retina of an eye of a patient;
capturing and recording at least one image of the plane of the retina resulting from the reflected light of said point light in the retina; and
analyzing said image by evaluating the light content thereof.

The method proposed by the second aspect of the invention comprises in a characteristic manner correcting low-order aberrations of the eye prior to said capture and recording, so that said image of the plane of the retina is free of the influence of said low-order aberrations, for which it comprises, though is not limited to, using the system proposed by the first aspect of the invention.

As a result of obtaining an image free of the influence of low-order aberrations, it is possible to discern between the different areas of the image, each of which is influenced by one cause or another. Specifically, and as discussed in the state of the art section, the peripheral area of the retinal image is influenced by the light scattering.

The proposed method comprises performing the mentioned analysis on a predetermined peripheral area and a predetermined central area of the retinal image, and establishing a ratio of the light energy contained in said areas. When establishing said ratio, rather than analyzing simply the peripheral area and taking an absolute value, the influence from the various conditions to which it is subjected or which are characteristic of the retina to be analyzed (ambient light conditions, conditions of different retinas from different patients, conditions of different sensitivities of the measurement apparatus, etc.) can be disregarded, since both areas, the central area and the peripheral area, will be influenced or affected equally by the different working conditions in which each measurement is performed, so by using the central area as reference, said influences will be compensated with respect to one another and, hence, will not affect the final ratio or measurement.

With respect to the mentioned light energy ratio, for a preferred embodiment it is an objective scattering index, OSI, calculated by applying the proposed method as a result of the ratio between the light energy $E_{ext}$ found in said peripheral area and the light energy $E_c$ found in said central area, according to the expression:

$$OSI = \frac{E_{ext}}{E_c}$$

The mentioned peripheral area preferably defines an annular area of the retinal image and the central area defines a circular area of the image, predetermined for example by means of using corresponding templates by processing means included in the system used for applying the proposed method and also responsible for analyzing the recorded image.

With respect to the dimensions of said predetermined areas, as for said annular area, it is demarcated by an inner circumference with a radius that is large enough to substantially not include residual high-order aberrations and by an outer circumference with a radius that is small enough to not include interference noise (for example caused by the measuring apparatus or system) and to not include areas without light signal, and as for said circular central area, it has a radius that is large enough to disregard the influence of possible artifacts and small enough to not include high-order aberrations.

For one embodiment, said annular area is demarcated by radii with arc lengths between 7 and 25 minutes, and said circular central area has a radius greater than 0.25 and less than 3 minutes of arc.

For one embodiment, the method comprises subtracting from said OSI a reference objective scattering index, OSIref, calculated from an image affected only by ocular aberrations, generated using aberration data of the eye obtained, for example, by means of using a Hartmann-Shack sensor.

For one embodiment, the method is applied to measuring intraocular scattering for the non-limiting purpose of diagnosing and evaluating cataracts.

For another embodiment, the method proposed by the second aspect of the invention is applied to measuring the tear film quality of said eye, for which it comprises performing said capture and recording for a plurality of sequentially ordered images of the plane of the retina obtained during a determined time period, keeping said projection of said point light beam on the retina without blinking.

Generally, said determined time period comprises a range including at least the time in which said tear film breaks up.

The images obtained in said sequence will be influenced by the tear film quality, the latter acting as a lens which allows the light to pass through it when it is in perfect condition, i.e., uniformly covering the cornea of the eye (immediately after a blink), and increasingly affecting the scattering of the point light beam projected in the retina as it gradually deforms until it breaks up, since a new blink does not occur.

For said embodiment, the method comprises calculating said objective scattering index, OSI, for each of said images of the plane of the retina of said plurality of images, and time ordering and evaluating the calculated OSI values in order to determine the tear film quality depending on how such values evolve.

By applying the proposed method, it is possible to measure the quality of artificial tears introduced in the eye of a patient, and compare them with that of a natural good-quality tear film.

As previously described, the method herein described is based on retrieving information on intraocular scattering which is located in the outermost part of double-pass images. For one embodiment, a particular object of the invention is the objective quantification of intraocular scattering by determining the objective scattering index (OSI). This index can be calculated using the ratio between the energy present in the outer part of the image and the central part thereof or, moving to the frequency domain, determining the area under the curve of the modulation transfer function, once the contribution of the low frequencies which do not provide information about intraocular scattering has been eliminated. The method described is robust, completely objective and the OSI can be used to classify patients with cataracts and select them for surgery.

The system or instrument uses as a nucleus a double-pass ophthalmoscopic system. In order to be able to determine intraocular scattering using the recorded double-pass image, it is necessary for it to be free of low-order aberrations (defocus, astigmatism). Therefore, the instrument must incorporate systems which allow correcting them.

Continuing with the description of the proposed system, for one embodiment the mentioned means for projecting a point light beam in the retina of an eye of a patient comprise: a point light source; a collimator system; a circular diaphragm which will perform the function of entrance pupil of the system; and a fixation test, the existence of which allows greater comfort for the patient and can consequently facilitate the measurements.

The point light source can be obtained by means of a laser or a light-emitting diode spatially filtered or coupled to an optical fiber.

For one embodiment, the recording means comprise image detectors suitable for recording an image of the plane of the retina.

For one embodiment, the system proposed by the first aspect of the invention comprises a diaphragm the diameter of which can be changed manually or automatically and which is conjugated with the actual pupil of the eye such that it acts like the effective exit pupil of the system.

For one embodiment, the system of the invention further comprises a plurality of beam splitters, a plurality of mirrors and a plurality of polarizing plates.

With the system proposed by the first aspect of the invention, using the recording of an image of the plane of the retina corrected for defocus and astigmatism, it is possible to determine the OSI by applying the method proposed by the second aspect, which allows quantifying the level of intraocular scattering of the eye in any type of applications of interest in ophthalmology, such as in the evaluation of the grade of cataracts, of the degree of opacification of the posterior capsule or of the degree of scattering after refractive surgery, as well as also quantifying the level of light scattering caused by the tear film, thus determining the quality thereof.

BRIEF DESCRIPTION OF THE DRAWINGS

To complement the description that is being made and for the purpose of aiding to better understand the features of the invention according to a preferred practical embodiment thereof, a set of drawings is attached as an integral part of said description in which the following has been depicted with an illustrative and non-limiting character.

DESCRIPTION OF A PREFERRED EMBODIMENT OF THE INVENTION

The invention herein described, relates to a system or apparatus (for measuring double-pass scattering) and an objective method for measuring ocular scattering. This method allows quantifying ocular scattering, both intraocular scattering and the scattering produced due to tear film quality, using double-pass images free of aberrations, in a robust manner, being able to be used in clinical practice. It provides a solution to a pending problem and differs from the methods known in the state of the art.

Figure 1:
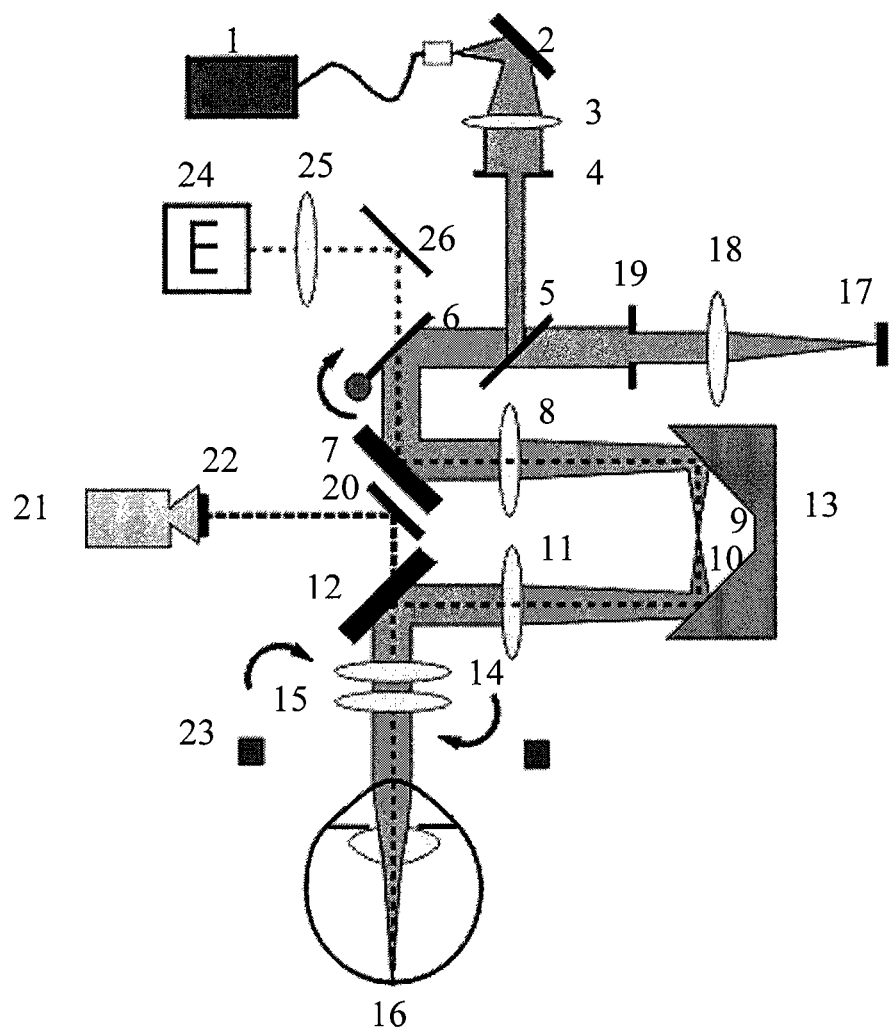
FIG. 1 shows the general scheme of the system proposed by the first aspect of the invention.

FIG. 1 shows a schematic diagram of the system of the present invention. The light from a laser diode coupled to an optical fiber 1 (or any other type of suitable light source, rather than using optical fiber the laser can be spatially filtered) is reflected in a mirror 2, collimated with a converging lens 3, passes through a diaphragm 4 and a beam splitter 5 before being reflected in a rotating beam splitter 6. In the described invention, the collimating lens has a focus of 100 mm but any other value can be used, taking into account that this value will influence the size of the point source on the retina. The rotating beam splitter 6 allows performing a small scan of the position in which the image is formed around the fovea, allowing the elimination of the speckle noise present in the images due to coherent light reflection in the retina. In the case of using a light-emitting diode as a light source, it would not be necessary to use the rotating mirror provided that the image does not have speckle noise.

The proposed system comprises means for correcting defocus aberrations comprising a system for allowing a focus correction including, as shown in FIG. 1:

first 9 and second 10 mirrors, each of which is opposite first 8 and second 11 lenses, such that the point light beam traverses said first lens 8, is reflected in said first mirror 9 and subsequently in said second mirror 10, after which it traverses said second lens 11, said first 9 and second 10 mirrors being assembled opposite one another on a mobile support 13, which can be moved closer to-farther from said lenses 8, 11 manually and/or automatically, to thus change the optical path between the first lens 8 and the second lens 11.

FIG. 1 shows how the light beam, after being reflected in the rotating beam splitter 6, is reflected in the mirrors 7, 9, 10, in the dichroic filter 12 and passes through the mentioned lenses 8 and 11. Since the mirrors 9 and 10 are assembled on the mentioned mobile support 13 they jointly form a system which allows correcting the spherical ametropia of the patient, previously referred to as focus corrector. In the event that the mobile support 13 can be moved automatically, it must be coupled to a motor which can be computer-controlled.

For another embodiment that is not shown, said means for correcting defocus aberrations comprise a system for allowing a focus correction including two lenses arranged in the path of said point light beam towards the eye of the patient, and can be moved closer to-farther from one another.

Continuing with the embodiment shown in FIG. 1, it can be seen in said figure how the beam finally passes through two cylindrical or spherotoric lenses 14 and 15 which can rotate with respect to one another manually and/or automatically and which allow neutralizing the astigmatism, to then enter the eye 16, said lenses 14, 15 being part of a system included in means for correcting astigmatism aberrations of the mentioned means for correcting low-order aberrations.

For another embodiment not shown, the mentioned means for correcting astigmatism aberrations comprise a system including a cylindrical lens which is interchangeable depending on the astigmatism of the patient.

In this invention, the foci of the lenses 8 and 11 are 100 mm but another value can be used. Cylindrical lenses 14 and 15 have powers of 1.5 Dioptres, allowing the neutralization of astigmatisms up to 3 Dioptres.

The entrance beam has a diameter of 2 mm, limited by a fixed circular aperture 4. This value has been chosen based on entering the eye with a very narrow beam. Other values could be chosen. The circular aperture could also be replaced with a diaphragm which allows manually or automatically changing the size of the incoming beam striking the eye 16. If the light source used emits a collimated beam, the system will do away with the optical fiber or the spatial filtering and collimating lens.

The system in question uses light from a laser diode 1 with a wavelength corresponding to near infrared (780 nm). However, any other wavelength of the visible spectrum (between 380 and 780 nm) could be used whether it comes from a coherent source such as a laser or the like, or from any other type of source, without needing to be monochromatic.

The optics of the eye make the incoming light striking the eye 16 converges in the retina and the image of a light point is formed. Part of the light reaching the retina is absorbed and part is back-reflected. A CCD camera 17 records said light. A lens 18 with a focus of 100 mm is used as a lens for this camera, but it could have another value, taking into account that it will influence the size of the image in the camera. The plane of the CCD is conjugated with the plane of the retina. Said camera integrates the energy reaching it during the exposure time. Any camera or system for recording images that can integrate alone or in association with a processing system, in a defined time period, by software or by hardware, the light reaching it can be used as a recording system.

In the outgoing path, the beam passes through the two lenses 14 and 15 neutralizing the astigmatism, through the focus corrector system 13, is reflected in the mirror 7 and in the rotating mirror 6, passes through the beam splitter 5 and through a circular aperture 19 before forming the image on the CCD camera 17.

The circular aperture 19 must be located such that it is conjugated with the pupil of the eye and will consequently act as the effective exit pupil of the system provided that its diameter is less than that of the pupil of the eye. To that end, the diameter of this circular aperture can be changed manually or automatically. It can be changed between 2 mm and 7 mm in the described invention.

In order to observe and align the pupil of the patient with the incoming beam, an auxiliary pupil control system formed by a mirror 20 and a CCD camera 21 is used. The lens 22 forms the image of the pupil in the camera. In the invention herein described, the focus used for the lens was 10 mm but it can be replaced with any other, taking into account that the dimensions will change and that this focus determines the size of the image of the pupil that the camera will record. If this image is digitalized and an algorithm is used which, using the gray levels of the image, is able to recognize the region corresponding to the pupil, the size of the latter can be measured. In order to visualize this image, the system incorporates a lighting system 23 for emitting light towards the region of the eye corresponding to the pupil of a type which does not influence the size of the pupil, particularly an infrared light.

The system uses infrared light emitting diodes (LED) with a wavelength of 900 nm. However, any type of source or any other wavelength could be used provided it corresponds to the infrared so that it does not influence the size of the pupil of the patient.

To facilitate fixation of the patient a fixation test 24 consisting of a letter the size of which corresponds to 20/20 visual acuity is used. This object is collimated by means of the lens 25 such that it is located in the infinite, like the light from the laser 1. After the light from the fixation test is reflected in a mirror 26, it passes through the beam splitter 6, is reflected in the mirror 7 and introduced in the focus corrector system and the astigmatism corrector system so that the patient can see it clearly. After the beam splitter 6 it follows the same path as the light from the laser 1 until reaching the retina of the patient. The system can work identically if it does not have the fixation test. However, having such test aids particularly in preventing unwanted accommodation effects and eye movements.

Figure 2:
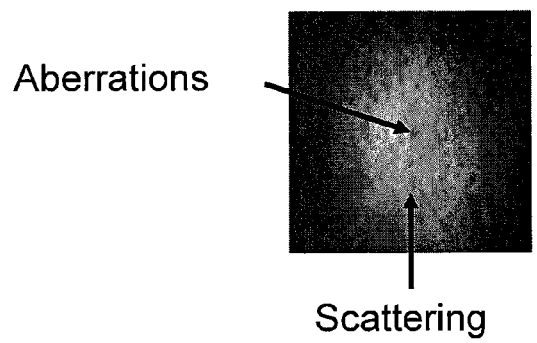
FIG. 2 shows a retinal image obtained with a double-pass system in which the area containing information about aberrations and the area containing information about intraocular scattering are shown.
Figure 3:
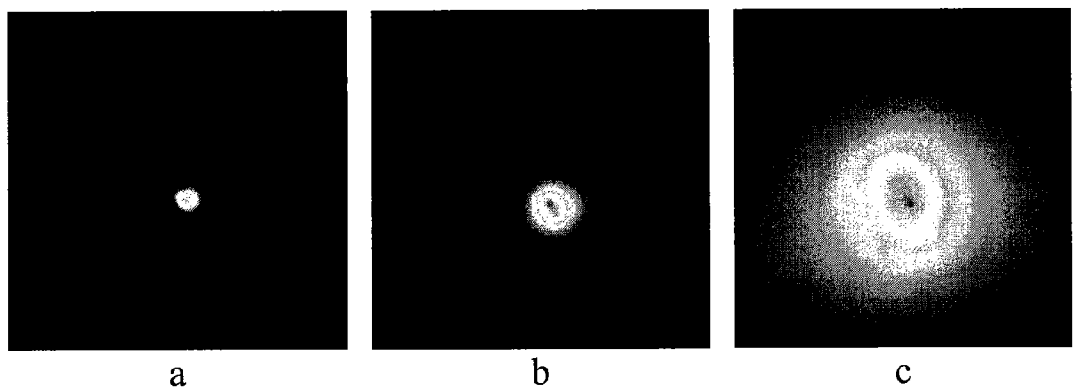
FIG. 3 shows an image of the plane of the retina for different grades of cataract: a) normal young eye; b) eye with a pre-cataract; c) eye with a mature cataract.

The retinal images obtained generally have information corresponding to the aberrations in the central area of the image and to intraocular scattering in the outer area, as shown in FIG. 2, representative of a retinal image obtained in a conventional manner. Nevertheless, in the case of the system of the invention the effect of the aberrations is minimized. FIG. 3 shows by way of example retinal images corresponding to different grades of cataract, obtained by means of the system and the method proposed by the invention. It specifically shows the image of a normal young eye (FIG. 3a), an eye with a pre-cataract (FIG. 3b) and an eye with a mature cataract (FIG. 3c).

The retinal image obtained with a double-pass system contains information about aberrations in the central part of the image and information about intraocular scattering on the outer part of the image (FIG. 2). The images obtained with the proposed system and method are free of low-order aberrations (defocus and astigmatism) such that the energy reaching the outer part of the image is only due to intraocular scattering (for the case in which the tear film does not influence light scattering).

As described above, the objective scattering index, OSI, is calculated as the ratio between the energy in an outer area of the image $E_{ext}$ and the energy of the central part of the image $E_c$ according to the expression (1):

$$OSI = \frac{E_{ext}}{E_c} \quad (1)$$

For the invention herein described, outer area has been considered as an annulus and the central area has been considered as a circle around the maximum of the image. The values of the radius of the annulus and of the circle can be any which reflect well the energy ratio between the outer and central part of the image. In order to have a reference free of scattering, it is possible to calculate the OSI for an image generated using the aberration data of the eye which can be obtained for example by performing the measurement with a Hartmann-Shack sensor for measuring ocular aberrations. This image is only affected by aberrations and consequently does not have any information about scattering. In this case, the OSI can be obtained, for example, as the result of a subtraction of the OSI of the double-pass image and the OSI of the aberration image.

Another possibility for calculating the objective scattering index is to do so in the frequency domain using the information contained in the modulation transfer function (MTF). To that end, the radial profile of the MTF is obtained and to minimize the effects of the information that the background of the image may contain which can be due to factors such as reflections and back-scattering, the function is normalized by eliminating the lowest frequencies. The area under the curve of normalized MTF can be computed as the OSI. In the present invention, normalization has been performed by eliminating information of the first two frequencies, but this number can be another number provided the factors which do not correspond to intraocular scattering are eliminated. In order to have a reference free of scattering, it is possible to calculate the OSI for the MTF of an image generated using the aberration data of the eye which can be obtained, for example, by performing the measurement with a Hartmann-Shack sensor for measuring ocular aberrations. This MTF is only affected by aberrations and consequently presents no information on scattering. In this case the OSI can be obtained, for example, as the result of a subtraction of the OSI of the double-pass MTF and the OSI of aberration MTF.

Figure 4A:
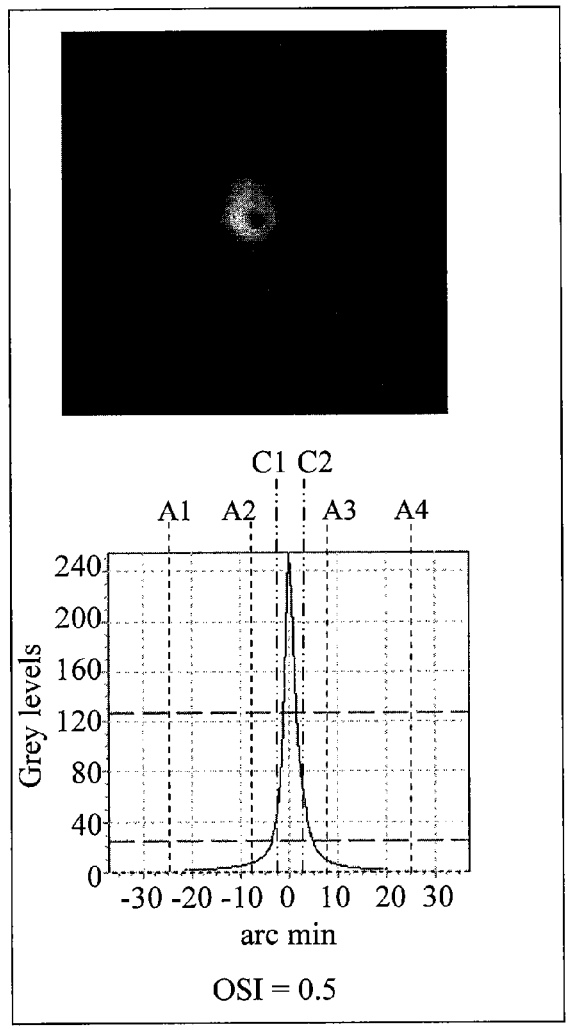
FIGS. 4a and 4b show retinal images, the radial profile thereof and OSI values obtained for the same eye when the low-order aberrations are corrected (FIG. 4a) and when they are not (FIG. 4b, for a defocus of 1.5 D and an astigmatism of 0.5 D).
Figure 4B:
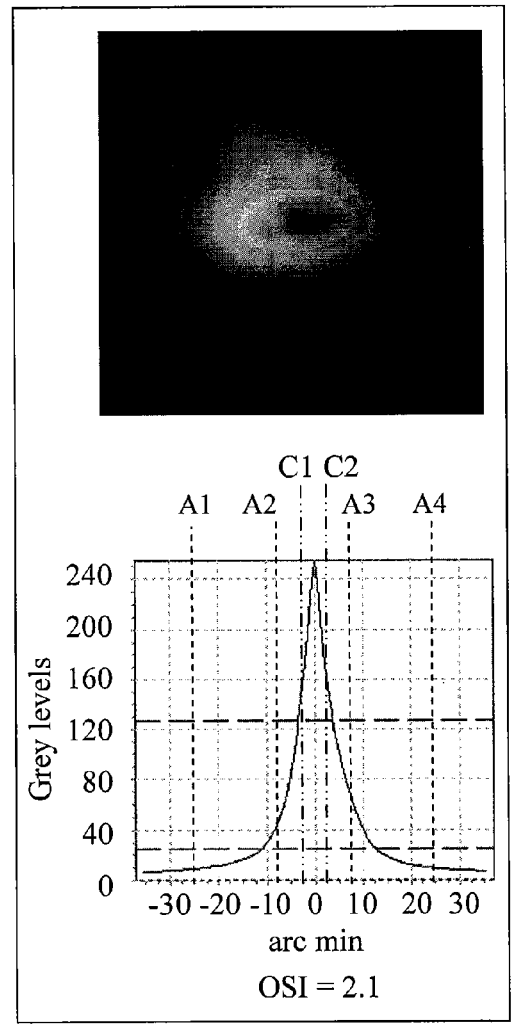

FIGS. 4a and 4b show two retinal images, together with the respective radial profile thereof and the OSI values obtained for the same eye when the low-order aberrations are corrected (FIG. 4a), OSI=0.5, and when they are not (FIG. 4b, for a defocus of 1.5 D and an astigmatism of 0.5 D), with an OSI=2.1.

In said radial profiles of FIGS. 4a and 4b, a section of the previously described areas to be analyzed of the image are indicated by means of a series of vertical lines, specifically the central area or circular area is demarcated by lines C1-C2, and the peripheral annular area by lines A1-A2 and A3-A4.

By comparing both radial profiles, it can be seen how the light energy in FIG. 4b (indicated as "gray levels" found in the image), is considerably, with respect to FIG. 4a, in the annular area, the section of which includes the portion of the wave demarcated between lines A1 and A2 and the portion included between lines A3 and A4. This is due to the fact that most of said energy is caused by low-order aberrations, which have not been corrected for the case shown in FIG. 4b, so the OSI=2.1 obtained for said case is not a reliable value of the objective measurement of scattering, and it is what would be obtained if the expression (1) was applied to an image obtained in a conventional manner, i.e., without correcting low-order aberrations.

Figure 5:
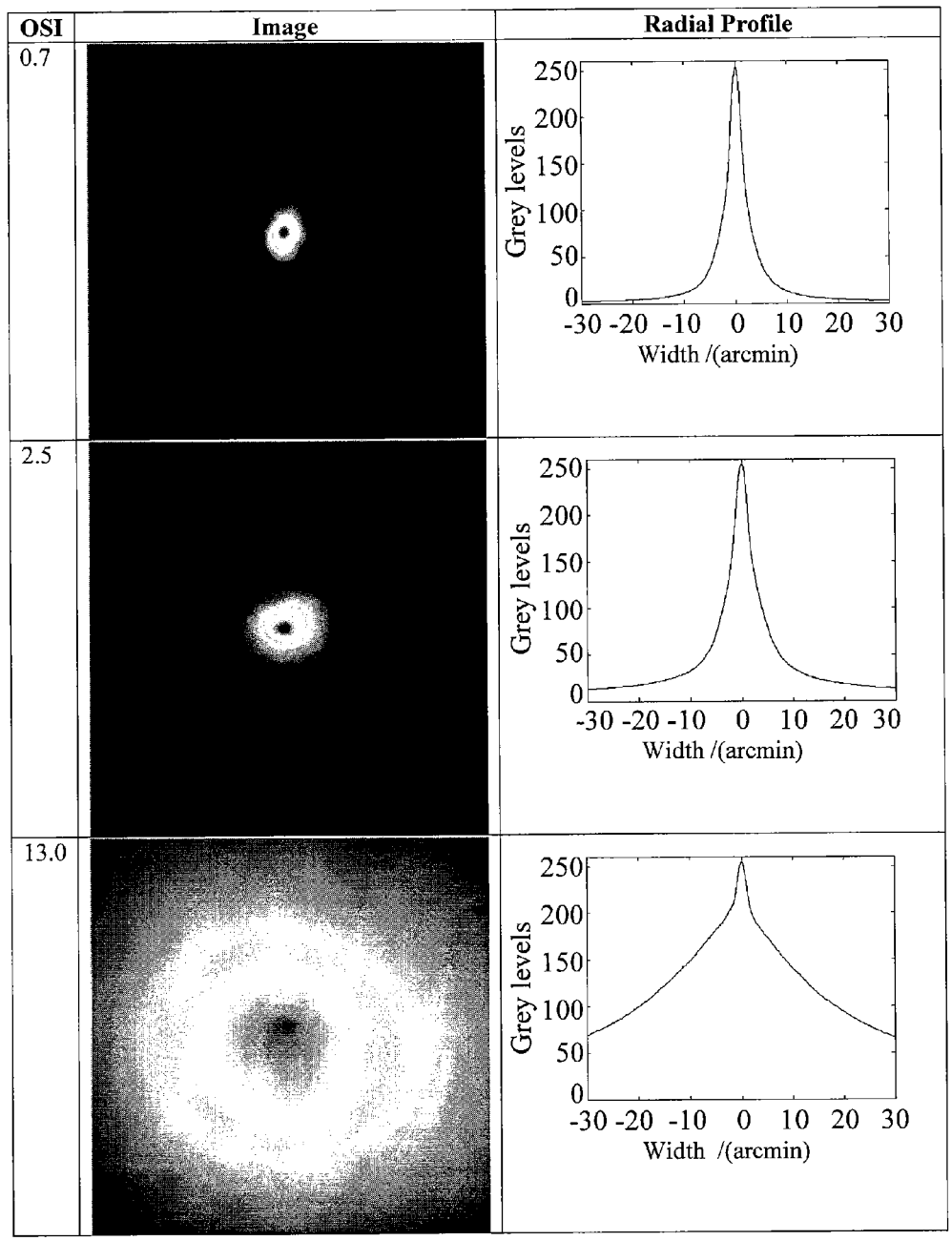
FIG. 5 show OSI values, retinal images and the radial profile thereof corresponding to different levels of cataract: normal young eye (top), eye with a pre-cataract (middle), eye with a mature cataract (bottom).

Now making reference to FIG. 5, different results obtained for three different eyes are shown, expressed by means of OSI values, retinal images and radial profiles thereof. Specifically, and ordered from top to bottom, for a normal young eye (OSI=0.7), an eye with a pre-cataract (OSI=2.7) and an eye with a mature cataract (OSI=13.0).

Figure 6:
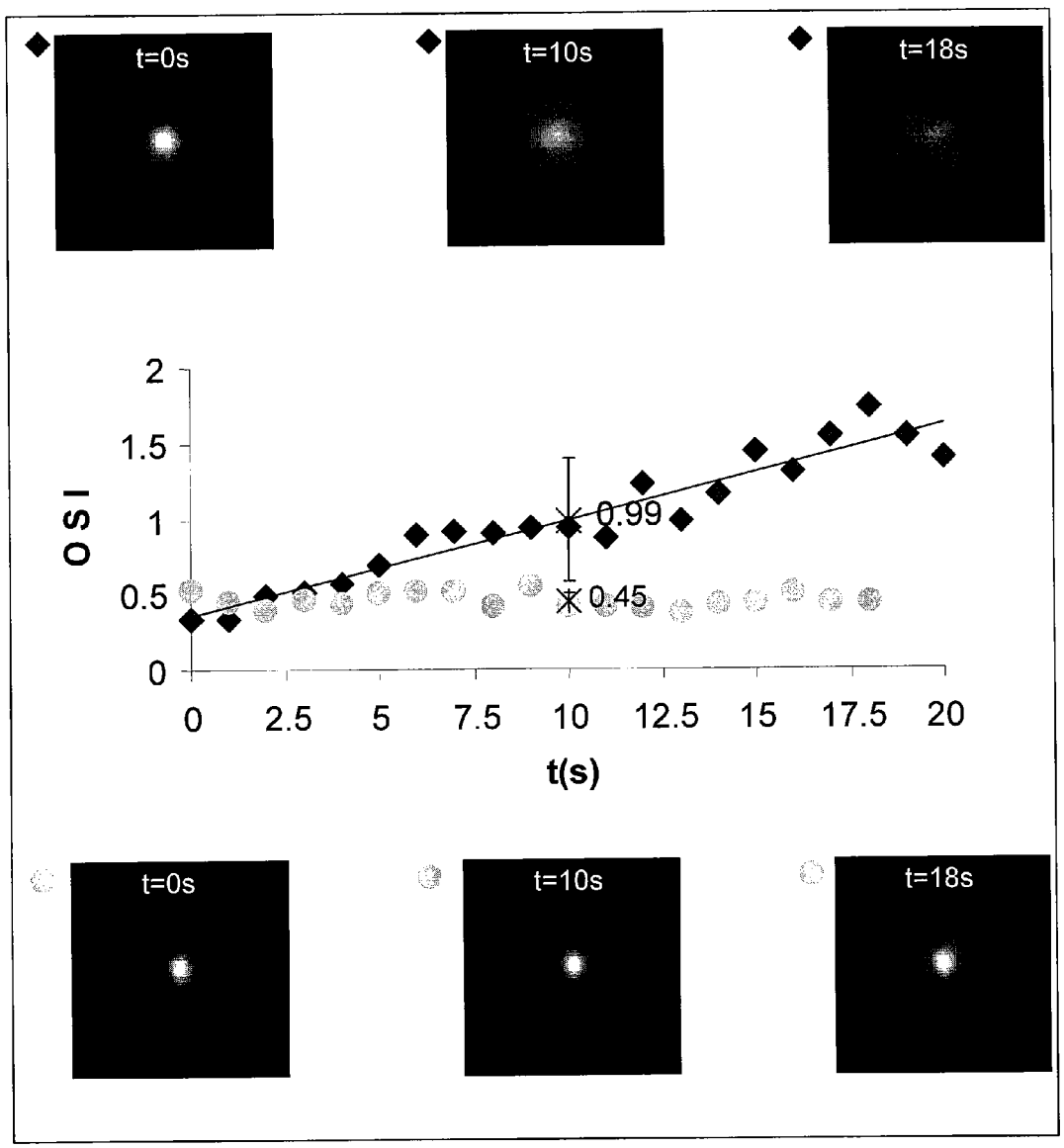
FIG. 6 shows time series of retinal double-pass images for an abnormal eye (top part), i.e., with poor tear film quality, and for a normal eye (bottom part), i.e., with good tear film quality. An OSI-time graph for both cases, abnormal eye and normal eye, is also shown.

Finally, FIG. 6 shows the previously described embodiment of the second aspect of the invention for which it is applied to measuring tear film quality. Specifically, said FIG. 6 shows two time series of retinal double-pass images for an abnormal eye (top part), i.e., with poor tear film quality, and for a normal eye (bottom part), i.e., with good tear film quality. The images have been taken for t=0 s, immediately after a blink, and for times of t=10 s and t=18 s, without blinking.

FIG. 6 also shows an OSI-time graph for both cases: abnormal eye and normal eye, in which a plurality of OSI values have been indicated, including those corresponding to the three images shown. Said graph shows how the evolution of the OSI values is maintained substantially uniform for the case of a tear film with good quality due to the fact that its influence with regard to light scattering of the point light beam in the retina is insignificant, i.e., it acts like a lens which allows the light beam to pass through it without altering its course. In contrast, the evolution of the OSI values for the case of a tear film with poor quality follows a downward course, which means that as the tear film deteriorates with time, its influence on scattered light is significant.

A person skilled in the art will be able to introduce changes and modifications in the embodiments described without departing from the scope of the invention as it is defined in the attached claims.

The invention claimed is:

1. A system for evaluating ocular health of a patient by measuring light scattering in the eyeball or eye region, of the type comprising:
    means for projecting a single, unpolarized point light beam in the retina of an eye of said patient, arranged to cause said single unpolarized point light beam to fall unpolarized on the retina of said eye of said patient;
    recording means for recording an image of the plane of the retina resulting from the reflected light of said point light beam in the retina;
    analysis means for analyzing said image by evaluating the light content thereof in order to perform said measurement of light scattering in the eyeball or eye region; and
    means for correcting low-order aberrations of the eye, including astigmatism aberrations, prior to said recording so that said image of the plane of the retina is absent of the influence of said low-order aberrations.

2. The system according to claim 1, wherein said means for projecting a point light beam and said recording means are part of a double-pass ophthalmoscopic system.

3. The system according to claim 2, wherein said means for correcting low-order aberrations are provided for also correcting defocus aberrations.

4. The system according to claim 1, wherein said means for correcting astigmatism aberrations comprise, in combination, two cylindrical or spherotoric lenses which are arranged in the path of said point light beam towards the eye of the patient, and which can rotate with respect to one another manually and/or automatically.

5. The system according to claim 1, wherein said means for correcting astigmatism aberrations comprise a cylindrical lens which is interchangeable depending on the astigmatism of the patient.

6. The system according to claim 1, comprising a system for visualizing the pupil of the patient for the purpose of aligning it with the point light beam, said system comprising at least one lighting system for emitting light towards the region of the eye corresponding to the pupil of a type which does not influence the size of the pupil, and a recording system formed by an image detector and its lens.

7. A method for evaluating ocular health of a patient by measuring light scattering in the eyeball or eye region, comprising:
    projecting, by using projecting means, a single, unpolarized point light beam on the retina of an eye of said patient, said single unpolarized point light beam falling unpolarized on the retina of said eye of said patient;
    capturing and recording, by using capturing and recording means, at least one image of the plane of the retina resulting from the reflected light of said point light beam in the retina; and
    analyzing, by using analysis means, said image by evaluating the light content thereof in a predetermined peripheral area, defining an annular area, and in a predetermined central area, defining a circular area, of said image, and calculating an objective scattering index, OSI, resulting from the ratio between the light energy, or $E_{ext}$, found in said peripheral area and the light energy, or $E_c$ found in said central area, according to the expression:

$$OSI = \frac{E_{ext}}{E_c}$$

wherein the method comprises correcting the low-order aberrations of the eye, including defocus and astigmatism, prior to said capture and recording, by using low-order aberrations correcting means, so that said image of the plane of the retina analyzed is absent of the influence of said low-order aberrations, in that said annular area is demarcated by an inner circumference with a radius to substantially not include residual high-order aberrations and by an outer circumference with a radius to not include interference noise and to not include areas without a light signal, and in that said circular central area has a radius to disregard the influence of possible artifacts and to not include high-order aberrations.

8. The method according to claim 7, wherein said annular area is demarcated by radii with arc lengths between 7 and 25 minutes, and said circular central area has a radius greater than 0.25 and less than 3 minutes of arc.

9. The method according to claim 7, further comprising subtracting from said OSI a reference objective scattering index, OSIref, calculated for an image affected only by ocular aberrations, generated using aberration data of the eye.

10. The method according to claim 9, further comprising obtaining said aberration data of the eye by means of using a Hartmann-Shack sensor.

11. The method according to claim 7, wherein the method is applied to measuring intraocular scattering.

12. The method according to claim 11, wherein the method is applied to diagnosing and evaluating cataracts.

13. The method according to claim 7, wherein the method is applied to measuring the tear film quality of said eye, for which it comprises performing said capture and recording for a plurality of sequentially ordered images of the plane of the retina obtained during a determined time period, keeping said projection of said point light beam on the retina without blinking.

14. The method according to claim 13, wherein said determined time period comprises a range including at least the time in which said tear film breaks up.

15. The method according to claim 13, further comprising calculating said objective scattering index, OSI, for each of said images of the plane of the retina of said plurality of images, and time ordering and evaluating the calculated OSI values in order to determine the tear film quality depending on how such values evolve.

16. A method for evaluating ocular health of a patient by measuring light scattering in the eyeball or eye region, comprising:
projecting, by using projecting means, a single, unpolarized point light beam on the retina of an eye of said patient, said single unpolarized point light beam falling unpolarized on the retina of said eye of said patient;
capturing and recording, by using capturing and recording means, at least one image of the plane of the retina resulting from the reflected light of said point light beam in the retina; and
analyzing, by using analysis means, said image by evaluating the light content thereof in a predetermined peripheral area, defining an annular area, and in a predetermined central area, defining a circular area, of said image, and calculating an objective scattering index, OSI, resulting from the ratio between the light energy, or $E_{ext}$, found in said peripheral area and the light energy, or $E_c$, found in said central area, according to the expression:

$$OSI = \frac{E_{ext}}{E_c}$$

wherein the method comprises correcting the low-order aberrations of the eye, including defocus and astigmatism, prior to said capture and recording, by using low-order aberrations correcting means, so that said image of the plane of the retina analyzed is absent of the influence of said low-order aberrations, in that said annular area is demarcated by an inner circumference with a radius to substantially not include residual high-order aberrations and by an outer circumference with a radius to not include interference noise and to not include areas without a light signal, and in that said circular central area has a radius to disregard the influence of possible artifacts and to not include high-order aberrations, and obtaining said image of the plane of the retina absent of the influence of low-order aberrations by means of using a system for measuring light scattering in the eyeball or eye region, of the type comprising:
means for projecting a single, unpolarized point light beam in the retina of an eye of a patient;
recording means for recording an image of the plane of the retina resulting from the reflected light of said point light in the retina;
analysis means for analyzing said image by evaluating the light content thereof in order to perform said measurement of light scattering in the eyeball or eye region; and
means for correcting low-order aberrations of the eye, including astigmatism aberrations, prior to said recording so that said image of the plane of the retina is absent of the influence of said low-order aberrations;
wherein said means for projecting a point light beam and said recording means are part of a double-pass ophthalmoscopic system, and
wherein said means for correcting low-order aberrations are provided for also correcting defocus aberrations.

17. A method for evaluating ocular health of a patient by measuring light scattering in the eyeball or eye region, comprising:
projecting, by using projecting means, a single, unpolarized point light beam on the retina of an eye of said patient, said single unpolarized point light beam falling unpolarized on the retina of said eye of said patient;
capturing and recording, by using capturing and recording means, information relating to the reflected light of said point light beam in the retina;
analyzing said information, by using analysis means, to perform said measurement of light scattering in the eyeball or eye region;
correcting low-order aberrations of the eye, including defocus and astigmatism, prior to said capture and recording, by using low-order aberrations correcting means, so that said information is absent of the influence of said low-order aberrations;
and using said analysis means for:
applying a modulation transfer function to said information and generating a radial profile of said modulation transfer function using the values obtained as a result of said modulation transfer function, to perform said analysis in the frequency domain;
normalizing said radial profile by eliminating the lowest frequencies corresponding to light information unrelated to ocular scattering; and
calculating the area existing under the curve of said normalized radial profile of said modulation transfer function, and determining an objective scattering index as a function of the calculated area.

* * * * *

UNITED STATES PATENT AND TRADEMARK OFFICE
CERTIFICATE OF CORRECTION

PATENT NO.       : 8,488,851 B2
APPLICATION NO. : 12/598834
DATED            : July 16, 2013
INVENTOR(S)      : Artal Soriano et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 763 days.

Signed and Sealed this
Eighth Day of September, 2015

Michelle K. Lee
*Director of the United States Patent and Trademark Office*